United States Patent
Barnhart et al.

(10) Patent No.: US 12,268,775 B2
(45) Date of Patent: *Apr. 8, 2025

(54) DISPENSING METHOD FOR PRODUCING DISSOLVABLE UNIT DOSE FILM CONSTRUCTS

(71) Applicant: ARx, LLC, Glen Rock, PA (US)

(72) Inventors: Scott D. Barnhart, York, PA (US); Eric Lakatosh, Red Lion, PA (US); William C. Baer, Harrisburg, PA (US); Abraham Anonuevo, Rosedale, MD (US)

(73) Assignee: ARx, LLC, Glen Rock, PA (US)

( * ) Notice: Subject to any disclaimer, the term of this patent is extended or adjusted under 35 U.S.C. 154(b) by 178 days.

This patent is subject to a terminal disclaimer.

(21) Appl. No.: 18/183,415

(22) Filed: Mar. 14, 2023

(65) Prior Publication Data

US 2023/0218513 A1 Jul. 13, 2023

Related U.S. Application Data

(63) Continuation of application No. 16/453,432, filed on Jun. 26, 2019, now Pat. No. 11,648,197.

(60) Provisional application No. 62/692,003, filed on Jun. 29, 2018, provisional application No. 62/691,327, filed on Jun. 28, 2018.

(51) Int. Cl.
*A61K 9/00* (2006.01)
*A61K 8/02* (2006.01)
*A61K 9/70* (2006.01)

(52) U.S. Cl.
CPC ............ *A61K 9/006* (2013.01); *A61K 8/0233* (2013.01); *A61K 9/0056* (2013.01); *A61K 9/7007* (2013.01)

(58) Field of Classification Search
CPC .... A61K 9/006; A61K 9/7007; A61K 9/0056; A61K 9/7015
See application file for complete search history.

(56) References Cited

U.S. PATENT DOCUMENTS

| | | | |
|---|---|---|---|
| 4,152,501 A | 5/1979 | Winter et al. | |
| 5,458,879 A | 10/1995 | Singh et al. | |
| 5,747,102 A | 5/1998 | Smith et al. | |
| 6,415,995 B1 | 7/2002 | Enderle et al. | |
| 7,470,397 B2 | 12/2008 | Meathrel et al. | |
| 8,056,827 B2 | 11/2011 | Xu | |
| 8,257,779 B2 | 9/2012 | Abernathy et al. | |
| 8,820,871 B2 | 9/2014 | Wallsten et al. | |
| 9,108,424 B2 | 8/2015 | Wallsten et al. | |
| 9,314,812 B2 | 4/2016 | Clark et al. | |
| 9,339,839 B2 | 5/2016 | Fliess et al. | |
| 9,457,935 B2 | 10/2016 | Fliess et al. | |
| 9,595,376 B2 | 3/2017 | Miyazaki et al. | |
| 9,676,184 B2 | 6/2017 | Wallsten et al. | |
| 9,789,511 B2 | 10/2017 | Aguilar et al. | |
| 9,904,298 B2 | 2/2018 | Fliess et al. | |
| 10,022,744 B2 | 7/2018 | MacIndoe et al. | |
| 10,059,098 B2 | 8/2018 | Wallsten et al. | |
| 10,138,916 B2 | 11/2018 | Fliess et al. | |
| 10,792,246 B2 | 10/2020 | Kakumanu et al. | |
| 2002/0013298 A1 | 1/2002 | Hunter | |
| 2002/0037919 A1 | 3/2002 | Hunter | |
| 2002/0148427 A1 | 10/2002 | Jones et al. | |
| 2005/0147653 A1 | 7/2005 | Yasuda et al. | |
| 2006/0153786 A1 | 7/2006 | Kochinke et al. | |
| 2006/0204591 A1 | 9/2006 | Burrell et al. | |
| 2006/0219735 A1 | 10/2006 | Faye et al. | |
| 2007/0154527 A1 | 7/2007 | Myers et al. | |
| 2007/0213393 A1 | 9/2007 | Hunter et al. | |
| 2007/0231271 A1 | 10/2007 | de Souza | |
| 2008/0026040 A1 | 1/2008 | Farr et al. | |
| 2008/0050422 A1 | 2/2008 | Myers et al. | |
| 2008/0153900 A1 | 6/2008 | Hunter | |
| 2009/0010992 A1 | 1/2009 | Palmer et al. | |
| 2009/0143390 A1 | 6/2009 | Cincotta | |
| 2010/0016450 A1 | 1/2010 | Lichter et al. | |
| 2010/0112050 A1 | 5/2010 | Ryoo et al. | |
| 2010/0150986 A1 | 6/2010 | Nagaso et al. | |
| 2011/0052699 A1 | 3/2011 | Funke et al. | |
| 2011/0182993 A1 | 7/2011 | Asari et al. | |

(Continued)

FOREIGN PATENT DOCUMENTS

| | | | |
|---|---|---|---|
| CN | 105536680 A | | 5/2016 |
| CN | 105732517 A | | 7/2016 |
| CN | 105944642 A | | 9/2016 |
| CN | 106268588 A | | 1/2017 |

(Continued)

*Primary Examiner* — Tracy Liu

(74) *Attorney, Agent, or Firm* — McNees Wallace & Nurick LLC

(57) ABSTRACT

Dissolvable unit dose film constructs are made by providing a muco-adhesive composition including a muco-adhesive polymer matrix in which the muco-adhesive polymer matrix has a water-soluble polymer, water-dispersible polymer, water-swellable polymer, or combinations thereof and a liquid carrier. The method further includes drying the muco-adhesive composition to remove at least a portion of the liquid carrier, forming a muco-adhesive film substrate, forming a composition for an active layer, the composition including a polymer matrix in which the polymer matrix for the active layer composition includes a water-soluble polymer, water-dispersible polymer, water-swellable polymer, or combinations thereof, an active ingredient and a liquid carrier. The method further includes depositing the composition for the active layer onto the muco-adhesive substrate as a plurality of individual volumes and removing the liquid carrier from the plurality of deposited individual volumes to form a plurality of dissolvable film active layers on the muco-adhesive substrate.

20 Claims, 6 Drawing Sheets

(56) References Cited

U.S. PATENT DOCUMENTS

| | | |
|---|---|---|
| 2011/0257141 A1 | 10/2011 | Carrara et al. |
| 2012/0269888 A1 | 10/2012 | Jetten et al. |
| 2012/0288566 A1 | 11/2012 | Friedman et al. |
| 2013/0035378 A1 | 2/2013 | Myers et al. |
| 2013/0142848 A1 | 6/2013 | Maeda et al. |
| 2013/0150410 A1 | 6/2013 | Lichter et al. |
| 2014/0248223 A1 | 9/2014 | Myers et al. |
| 2014/0272099 A1 | 9/2014 | Braun et al. |
| 2014/0377312 A1 | 12/2014 | Krumme et al. |
| 2015/0165046 A1 | 6/2015 | Ruegger et al. |
| 2015/0314000 A1 | 11/2015 | Rosenberg et al. |
| 2016/0008293 A1 | 1/2016 | Shi et al. |
| 2016/0089327 A1 | 3/2016 | Khusial et al. |
| 2016/0089328 A1 | 3/2016 | Giovinazzo et al. |
| 2016/0279134 A1 | 9/2016 | Kohr et al. |
| 2016/0303038 A1 | 10/2016 | Yadav et al. |
| 2016/0310415 A1 | 10/2016 | Lichter et al. |
| 2017/0042830 A1 | 2/2017 | Myers et al. |
| 2017/0056374 A1 | 3/2017 | Lee et al. |
| 2017/0087084 A1 | 3/2017 | Musho et al. |
| 2017/0209431 A1 | 7/2017 | Myers et al. |
| 2017/0246108 A1 | 8/2017 | Musho et al. |
| 2017/0252294 A1 | 9/2017 | Musho et al. |
| 2017/0290776 A1 | 10/2017 | Schobel et al. |
| 2017/0290777 A1 | 10/2017 | Yang et al. |
| 2017/0290807 A1 | 10/2017 | Mundada et al. |
| 2017/0348251 A1 | 12/2017 | Schobel et al. |
| 2018/0008595 A1 | 1/2018 | Oksche et al. |
| 2018/0092979 A1 | 4/2018 | Li et al. |
| 2018/0104195 A1 | 4/2018 | Schobel et al. |
| 2018/0133146 A1 | 5/2018 | Barnhart et al. |
| 2018/0140559 A1 | 5/2018 | Fuisz et al. |
| 2018/0177741 A1 | 6/2018 | Yang et al. |
| 2018/0200198 A1 | 7/2018 | Schobel et al. |
| 2018/0296496 A1 | 10/2018 | Myers et al. |
| 2019/0000833 A1 | 1/2019 | Finn et al. |
| 2019/0015320 A1 | 1/2019 | Morales et al. |
| 2019/0091281 A1 | 3/2019 | Wargacki et al. |

FOREIGN PATENT DOCUMENTS

| | | |
|---|---|---|
| CN | 106822058 A | 6/2017 |
| CN | 106852916 A | 6/2017 |
| CN | 106852917 A | 6/2017 |
| CN | 107412200 A | 12/2017 |
| CN | 107774199 A | 3/2018 |
| CN | 107803167 A | 3/2018 |
| CN | 108031411 A | 5/2018 |
| CN | 108785278 A | 11/2018 |
| CN | 108785281 A | 11/2018 |
| CN | 108785282 A | 11/2018 |
| CN | 108785285 A | 11/2018 |
| CN | 108926547 A | 12/2018 |
| JP | 2006528192 A | 12/2006 |
| JP | 2008538782 A | 11/2008 |
| JP | 2013525394 A | 6/2013 |
| JP | 2013537200 A | 9/2013 |
| JP | 2013540161 A | 10/2013 |
| JP | 2017001956 A | 1/2017 |
| JP | WO2014104149 A1 | 1/2017 |
| KR | 20110041412 A | 4/2011 |
| WO | 2007053608 A2 | 5/2007 |
| WO | 2007067494 A1 | 6/2007 |
| WO | 2009023877 A2 | 2/2009 |
| WO | 2010077156 A1 | 7/2010 |
| WO | 2014116770 A1 | 7/2014 |
| WO | 2015117004 A1 | 8/2015 |
| WO | 2017027528 A1 | 2/2017 |
| WO | 2018094037 A1 | 5/2018 |
| WO | 2019016814 A1 | 1/2019 |

DISPENSING METHOD FOR PRODUCING DISSOLVABLE UNIT DOSE FILM CONSTRUCTS

CROSS-REFERENCE TO RELATED APPLICATIONS

This application is a continuation of and claims the benefit of, and priority to, U.S. Non-Provisional application Ser. No. 16/453,432, entitled "Dispensing Method for Producing Dissolvable Unit Dose Film Constructs," which was filed on Jun. 26, 2019 and which issued as U.S. Pat. No. 11,648,197 B2 on May 16, 2023, which claims the benefit of, and priority to, U.S. Provisional Application No. 62/692,003, entitled "Dispensing Method for Producing Dissolvable Unit Dose Film Constructs," which was filed on Jun. 29, 2018 and U.S. Provisional Application No. 62/691,327, entitled "Dispensing Method for Producing Dissolvable Unit Dose Film Constructs," which was filed on Jun. 28, 2018, all of which are hereby incorporated by reference in their entirety.

FIELD

The present application is directed toward the field of thin films and more particularly to methods for producing dissolvable unit dose film constructs used for drug delivery.

BACKGROUND

Fast-dissolving drug-delivery systems were first developed in the late 1970s as an alternative to tablets, capsules, and syrups for pediatric, geriatric and other patients who experience difficulties swallowing traditional oral solid-dosage forms. In response to this need, a variety of orally disintegrating tablet (ODT) formats were commercialized. Most ODT products were formulated to dissolve in less than one minute when exposed to saliva to form a solution that could then be more easily swallowed.

More recently, dissolvable oral thin films (OTFs) emerged from the confection and oral care markets in the form of breath strips. These products became a widely accepted form by consumers for delivering vitamins and personal care products and subsequently for also delivering other active ingredients, including pharmaceuticals.

Pharmaceutical companies and consumers alike have embraced OTFs as a practical and accepted alternative to traditional medicine forms such as liquids, tablets, and capsules. OTFs offer fast, accurate dosing in a safe, efficacious format that is convenient and portable, without the need for water or measuring devices. OTFs are typically the size of a postage stamp and disintegrate on a patient's tongue in a matter of seconds for the rapid release of one or more active pharmaceutical ingredients (APIs). More broadly, the use of thin films has expanded to include a variety of products that are manufactured and used for a wide range of transmucosal drug delivery within the oral cavity as well as via other mucosal interfaces.

Despite the move toward drug delivery by thin films, numerous drawbacks and disadvantages still exist with such products and there are a variety of commercial needs in the field that have not yet been met.

SUMMARY

Exemplary embodiments are directed to films for oral and transmucosal drug delivery including, but not limited to, dissolvable oral thin films, dissolvable transmucosal thin films, and the production of the same that address currently existing but unmet needs. More particularly, exemplary embodiments are directed to dissolvable unit dose film constructs.

In one exemplary embodiment, dissolvable unit dose film constructs are made by providing a muco-adhesive composition including a muco-adhesive polymer matrix in which the muco-adhesive polymer matrix has a water-soluble polymer, water-dispersible polymer, water-swellable polymer, or combinations thereof, and a liquid carrier. The method further includes drying the muco-adhesive composition to remove at least a portion of the liquid carrier, forming a muco-adhesive film substrate, forming a composition for an active layer, the composition including a polymer matrix in which the polymer matrix for the active layer composition includes a water-soluble polymer, water-dispersible polymer, water-swellable polymer, or combinations thereof, an active ingredient, and a liquid carrier, wherein the composition for the active layer has a viscosity of at least 25 cps at 1 $\sec^{-1}$ shear rate. The method further includes depositing the composition for the active layer onto the muco-adhesive substrate as a plurality of individual volumes and removing the liquid carrier from the plurality of deposited individual volumes to form a plurality of dissolvable film active layers on the muco-adhesive substrate.

In another exemplary embodiment, a method for forming a dissolvable unit dose film construct, includes providing a muco-adhesive composition including a muco-adhesive polymer matrix. The muco-adhesive polymer matrix includes a water-soluble polymer, a water-dispersible polymer, a water-swellable polymer, or combinations thereof, and a liquid carrier. The method further includes drying the muco-adhesive composition to remove at least a portion of the liquid carrier, forming a muco-adhesive film substrate, forming a composition for active layer, the composition having at least 5% by weight solids and viscosity between 300 and 2,000 cps at 1 $\sec^{-1}$ shear rate. The composition for the active layer includes a water-soluble polymer, a water-dispersible polymer, a water-swellable polymer, or combinations thereof, and active ingredient, and a liquid carrier. The method further includes dispensing the composition for the active layer onto the muco-adhesive substrate via a jetting system having a piezoelectric or air actuated valve as a plurality of individual volumes each having a volume between 0.1 µL and 50 µL, removing the liquid carrier from the plurality of deposited individual volumes to form a plurality of dissolvable film active layers on the muco-adhesive substrate, and cutting the muco-adhesive film substrate to separate at least some of the plurality of dissolvable film active layers and thereby form individual unit doses.

In some exemplary embodiments, the composition for the active layer is deposited onto the muco-adhesive substrate as a plurality of individual volumes in the range between 0.1 µL to 5,000 µL, such as a plurality of individual volumes in the range between 0.1 µL and 50 µL; the composition for the active layer deposited onto the muco-adhesive substrate has a viscosity between 25 and 5,000 cps at 1 $\sec^{-1}$ shear rate, such as between 300 and 2,000 cps at 1 $\sec^{-1}$ shear rate; and/or the composition for the active layer is at least 5% by weight solids at the time of depositing.

In certain embodiments, active layers are applied on opposing sides of the muco-adhesive substrate, such as two layers containing the same active ingredient or two layers containing different active ingredients.

BRIEF DESCRIPTION OF THE DRAWINGS

Whenever possible, the same reference numbers will be used throughout the drawings to represent the same parts.

DETAILED DESCRIPTION OF EXEMPLARY EMBODIMENTS

Figure 1:
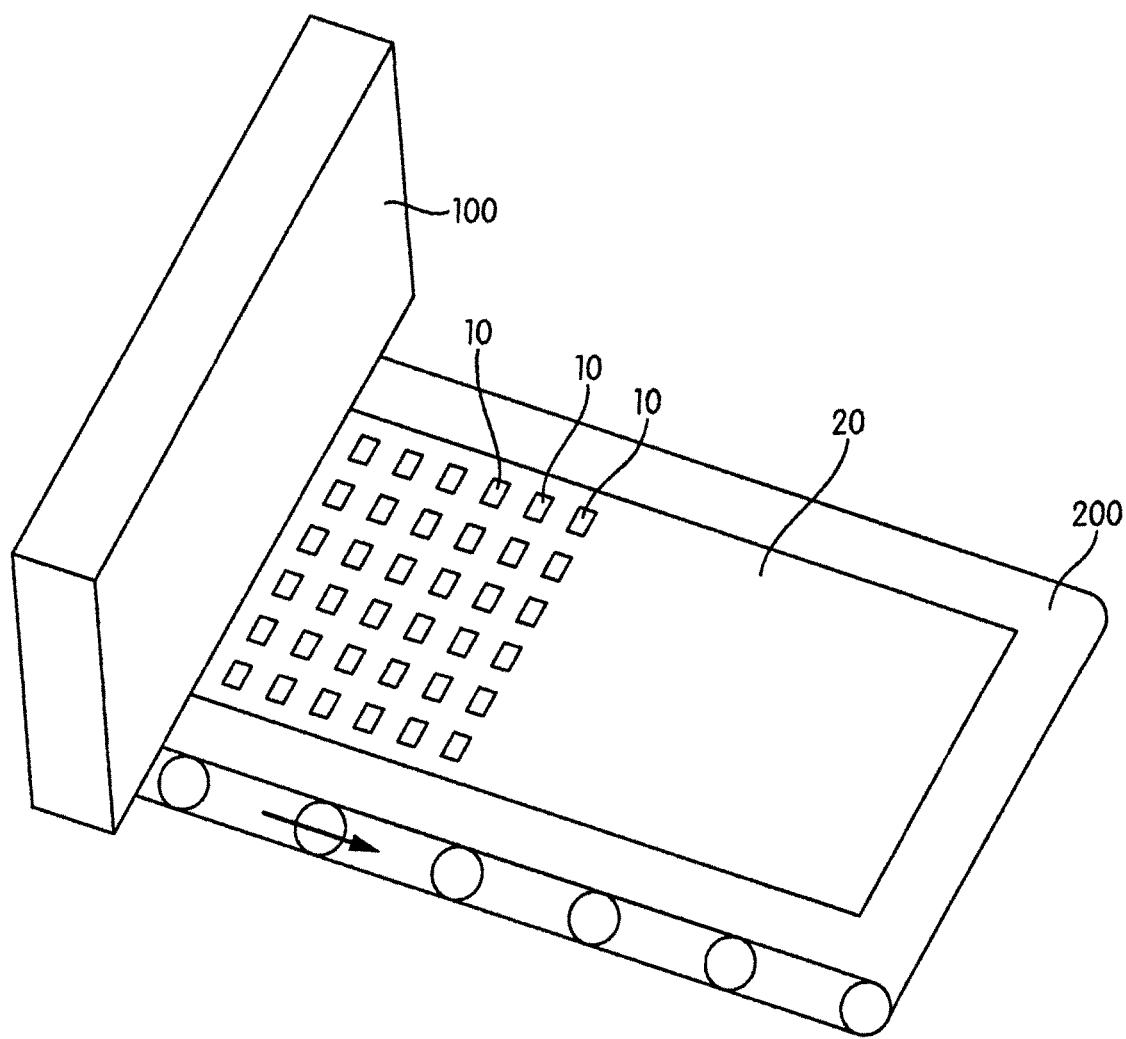
FIG. 1 illustrates an exemplary system for producing dissolvable unit dose film constructs, according to an embodiment of the present disclosure.

Provided are methods of producing dissolvable unit dose film constructs used for drug delivery. Embodiments of the present disclosure, in comparison to methods not including one or more of the features disclosed herein, include the ability to incorporate multiple active ingredients into a single dissolvable unit dose film construct, even if those active ingredients would otherwise be incompatible with one another, through discrete deposition of those active ingredients at isolated locations on a common carrier matrix, the ability to deposit a high concentration of active ingredients onto a single dissolvable unit dose film construct, even if the active ingredient would otherwise be incompatible with the dissolvable film carrier, through discrete deposition of the active ingredient at isolated locations on a common carrier matrix, or combinations thereof.

Referring to FIGS. 1-5, in one embodiment, a method for forming a dissolvable unit dose film construct 10 includes providing a muco-adhesive composition including a polymer matrix, wherein the polymer matrix includes a water-soluble polymer, a water-dispersible polymer, a water-swellable polymer, or combinations thereof, and a liquid carrier. The muco-adhesive composition is dried to remove at least a portion of the liquid carrier, forming a dissolvable muco-adhesive substrate 20.

A dissolvable composition for providing a dissolvable active layer 12 on the substrate 20 is formed that includes a polymer matrix, an active ingredient, and a liquid carrier. Like the substrate 20, the polymer matrix for the dissolvable active layer 12 is a film-forming matrix and is a liquid-base biologically compatible film forming matrix that includes a water-soluble polymer, a water-dispersible polymer, a water-swellable polymer, or combinations thereof. The polymers for the composition that forms the active layer 12 may be the same or different as that used to form the muco-adhesive substrate 20. The dissolvable composition to form the active layer 12 is deposited onto the muco-adhesive substrate 20 as a plurality of individual dosage units and at least a portion of the liquid carrier is removed to form the plurality of dissolvable active layers 12.

In some embodiments, the muco-adhesive composition of the substrate 20 may also include an active ingredient. The active ingredient of the muco-adhesive composition may be the same as the active ingredient of the dissolvable composition that forms the active layer 12 or may be compositionally distinct from the active ingredient of that layer.

In one embodiment, the muco-adhesive substrate 20 is formed as a continuous web onto which the plurality of active layers 12 are applied, then cut into individual units 10 for subsequent packaging. In another embodiment, the muco-adhesive substrate 20 is formed as a continuous web that is cut into individual units 10 prior to applying the active layer 12 to the muco-adhesive substrate 20. In still another embodiment, the muco-adhesive composition is formed to provide the muco-adhesive substrate 20 directly as individual units, such as stenciling a thixotropic paste onto a carrier.

Known methods of dissolvable film production involve casting the liquid formulation as a continuous film, sheet or web in the form of wide and long rolls on a continuous substrate (e.g., paper or polyester liners which may or may not have release coatings) to form what is sometimes referred to as a master roll. The manufacturing process includes drying the liquid formulation to remove solvents (aqueous and/or non-aqueous) to yield the thin film on the substrate. The master rolls thus formed are then converted into smaller unit doses through a combination of roll slitting and individual unit dose die-cutting, as well as transferring those doses from the manufacturing substrate to the product's primary packaging.

Unlike conventional methods of forming dissolvable thin films as a cast sheet that is subsequently cut into smaller unit doses, the present dissolvable unit dose film constructs 10 may be created by direct deposition of the active liquid formulation onto a continuous polymer film matrix or onto discrete film units, in either case forming individual single unit dose films. Among other advantages, the use of individually formed doses may limit variation of the active ingredient between dissolvable unit dose film constructs 10 that may occur across the web as a result of coating thickness variations in conventional master roll formation. This may help ensure that a relatively more precise and consistent volume of formulation and active ingredient is deposited, directly forming smaller-scale, single unit doses.

In certain embodiments, depositing an active ingredient onto a film in a unit dose form is accomplished by direct dispensing as described in more detail herein.

Broadly, methods for depositing dissolvable compositions including active ingredients onto muco-adhesive substrates 20 in a unit dose form may employ dispensing a small volume of the dissolvable composition used to form the active layer 12 of at least 0.1 µL up to about 5,000 µL, in some embodiments up to about 500 μL such as up to about 100 μL including up to about 50 μL directly onto a surface of the muco-adhesive substrates 20. In some embodiments the amount dispensed is between 0.1 μL and about 10 μL, such as about 0.1 μL, 0.5 μL, 1 μL, 2 μL, 3 μL, 4 μL, 5 μL or any other amount up to about 10 μL, 20 μL, 30 μL, 40 μL, 50 μL, 100 μL and greater up to about 500 μL or even as high as 5,000 μL and any range or subrange of any of the foregoing. In some embodiments, the entire volume is dispensed in a single step, although for total volumes higher than 10 μL, it may be desirable to serially dispense multiple iterations of smaller volumes adjacent and/or overlying one another to form the active layer 12. In some embodiments, decreasing the volume of each dispensing volume to achieve the same unit dose with more total dispensing actions has increased precision and repeatability of the unit dose amount relative to fewer dispensing actions of larger volume. Without being bound by theory, it is believed that the higher number of dispensing actions may average out random variability in each dispensing volume.

In contrast, conventional inkjet printing used in conventional printing techniques dispenses drop volumes on the order of 2 to 20 μL, and as such requires very low viscosities to make such small drop sizes. The use of such conventional techniques in film formation as described herein is impractical for commercial production and furthermore, would limit the amount of active ingredient and other solid content that could be used. Compositions applied in accordance with exemplary embodiments are typically 5% by weight solids or greater of a high viscosity blend, such as 10% by weight solids or greater, such as 15% by weight solids or greater.

The dissolvable compositions including active ingredients may be dispensed from a dispenser head by a force that moves the liquid from a reservoir in, or connected to, the dispenser head to the surface of the substrate. This may advantageously be achieved by jetting through the dispensing head positioned over the substrate. The substrate may be a continuous polymer film sheet, a single unit polymer film, or other material that serves both as a surface onto which the dissolvable compositions including active ingredient may be deposited as well as form part of the final dissolvable unit dose film constructs 10, eliminating the need for a transfer sheet. The dispenser head is typically, but not necessarily, a needle-like tip.

Jetting devices are described in U.S. Pat. No. 9,789,511 to Aguilar et al., which is incorporated by reference in its entirety as if fully-restated herein. In general, a "jetting device" is a device which ejects, or "jets," a droplet of material from a dispenser nozzle to land on a substrate, and wherein the droplet disengages from the dispenser nozzle before making contact with the substrate. Thus, in a jetting process, the droplet dispensed is "in-flight" between the dispenser and the substrate, and not in contact with either the dispenser or the substrate for at least a part of the distance between the dispenser and the substrate. U.S. Pat. No. 9,789,511 at col. 1, lines 12-21. Jetting devices and jetting processes are further described in U.S. Pat. No. 8,257,779 to Abernathy et al. which is incorporated by reference in its entirety as if fully-restated herein.

The dissolvable compositions including active ingredients may also be dispensed through a jetting system using a piezoelectric or air actuated valve. Piezoelectric systems involve applying electrical charge to a piezo material that expands and contracts to control the flow of the dissolvable compositions including active ingredients, while air-actuated systems use air pressure to control the valve. This non-contact type of dispensing is defined by the ability to dispense the dissolvable compositions including active ingredients without the need for the dispenser head to move in the Z-axis and touch the substrate, thereby allowing for a faster and more precise process. Frequencies of 1-3,000 Hz is typically, but not necessarily, the operating range for valves used in the deposition processes. Piezoelectric actuated valves are described in U.S. Pat. No. 10,022,744 to MacIndoe et al., which is incorporated by reference in its entirety as if fully-restated herein.

The geometry of the deposition of dissolvable compositions including active ingredients formed by direct dispensing may be of any type. In some embodiments, the geometry may be a circular shape, as will occur by expressing the formulation from a cylindrical tip in which the surface energy of the substrate surface is uniform. In accordance with other embodiments, square, rectangle, or even more complex polygon shapes may be employed. This may be achieved by providing a dispenser head in which the formulation exits the head and is pinned between the head and target surface to establish the desired shape. In this manner, the liquid fills a gap (typically about 1 mm high) between the substrate and the dispenser head. Thus, if the geometry of the dispense head's surface closest to the substrate is rectangular, then a rectangular deposit is generated.

Alternatively, a single unit dose may be formed by repeated smaller dispensing cycles from one or more dispensing units. Each dispenser head may be attached to a robotic arm that controls where the dissolvable compositions, including active ingredients, is deposited on the substrate. Alternatively, the platform on which the substrate is mounted may be motorized to move the substrate as the formulation is being dispensed from a fixed dispenser head. These configurations afford the ability to vary the size and shape of the dose as needed.

The modular design of jetting systems for microdeposition allows for easy customization of the equipment to satisfy deposition requirements. Dispensing nozzles and liquid reservoirs may be interchanged for different sizes or geometries. This modular design, in which the actuator is isolated from the parts that are in contact with the active ingredient, also allows for easier equipment cleaning, sanitization, and service.

It will be appreciated that other ways may also be employed to dispense dissolvable compositions of varying geometries. By way of example, the surface energy of the substrate may be modified to result in better wetting by the dispensed formulation. In one embodiment, a corona—or plasma-treatment using a mask with openings of the geometry to be obtained provides a well-defined region on the substrate surface of increased surface energy that promotes fluid migration to cover the treated area. In another embodiment, the surface energy of the formulation being dispensed may be modified or tailored to achieve a desired flow characteristic during and after dispensing. In yet another embodiment, a dam or frame in the desired geometry is provided on the substrate surface, followed by dispensing the dissolvable composition from the dispensing head into the defined area to generate a deposit with a specific geometry and uniformity.

Jetting systems also have the ability to dispense a repeatable low deposition volume in the nanoliter range and can dispense multiple dots to achieve a larger deposition volume. In some embodiments, the practical limitations on total maximum dispensed volume, for continuous manufacturing of individual dissolvable unit dose film constructs 10 is about 0.5 mL.

It will be appreciated that the fluid characteristics of the formulation being dispensed may impact the ability to consistently obtain uniform film dispensing. The fluid viscosity of the formulation used to form the active layer 12 and any other layers that are dispensed on the mucoadhesive substrate 20 is in the range of 25 to 100,000 cps at 1 sec$^{-1}$ shear rate, with higher viscosities better accomplished by changing the nozzle geometry and heating the fluid, and lower viscosities preferred for ambient-temperature jetting techniques. The particular viscosity of the active formulation within this range may vary depending on a variety of factors depending on the characteristics of the deposition to be created, including how the formulation is desired to behave after it is dispensed onto the substrate, which itself may be a function of how a particular geometry is to be obtained. For example, pinning the formulation so that it does not spread beyond the intended area may be influenced by the formulation's viscosity, as well as its surface tension and the substrate's surface energy. Generally, the viscosity of the composition applied to form the active layer 12 is between 25 and 5,000 cps at 1 sec$^{-1}$ shear rate, such as about 30, 40, 50, 75, 100, 200, 300, 400, 500, 600, 700, 800, 900, 1,000, 2,000, 3,000, or 4,000 cps at 1 sec$^{-1}$ shear rate, and any range or subrange of any of the foregoing, such as, for example, between 500 and 800 cps at 1 sec$^{-1}$ shear rate. In some embodiments, it will be appreciated that the viscosity of the composition applied to form the active layer 12 may be as low as 1 cps at 1 sec$^{-1}$ shear rate.

PCT/US2016/046217 assigned to Purdue Research Foundation (Purdue) describes Methods and Systems for Depositing Active Ingredients on Substrates. Active ingredients are delivered as fluids to a fluid-dispensing device for the creation of one or more drops for deposition onto substrates such as for the creation of microdoses. Purdue describes various methods and apparatus to dispense a fluid containing an active ingredient onto a substrate, but does not disclose critical process controls required in order to repeatedly and reproducibly deposit liquids that meet pharmaceutical standards, such as content uniformity, and does not provide guidance to develop such process controls. Purdue identifies in paragraph [0045] that drop dynamics are affected by surface tension and viscosity, and teaches that viscosity is preferred to be less than about 20 mPas, and utilizes positive displacement pumps to aid in drop ejection.

The viscosity of the formulations may be increased or decreased by temperature, which can affect the quality of the deposition. Heating the formulation in the holding vessel prior to dispensing or dispensing the formulation through a heated nozzle usually decreases the liquid viscosity and can improve the deposition quality. The temperature of the formulation should not be heated beyond the degradation temperature of the active ingredient or the temperature should be sufficiently low to avoid boiling the solvent of the formulation. In one embodiment, the formulations may be increased in temperature as the formulations exit the nozzle, which may reduce the dwell time of heat applied to the formulations.

Figure 9:
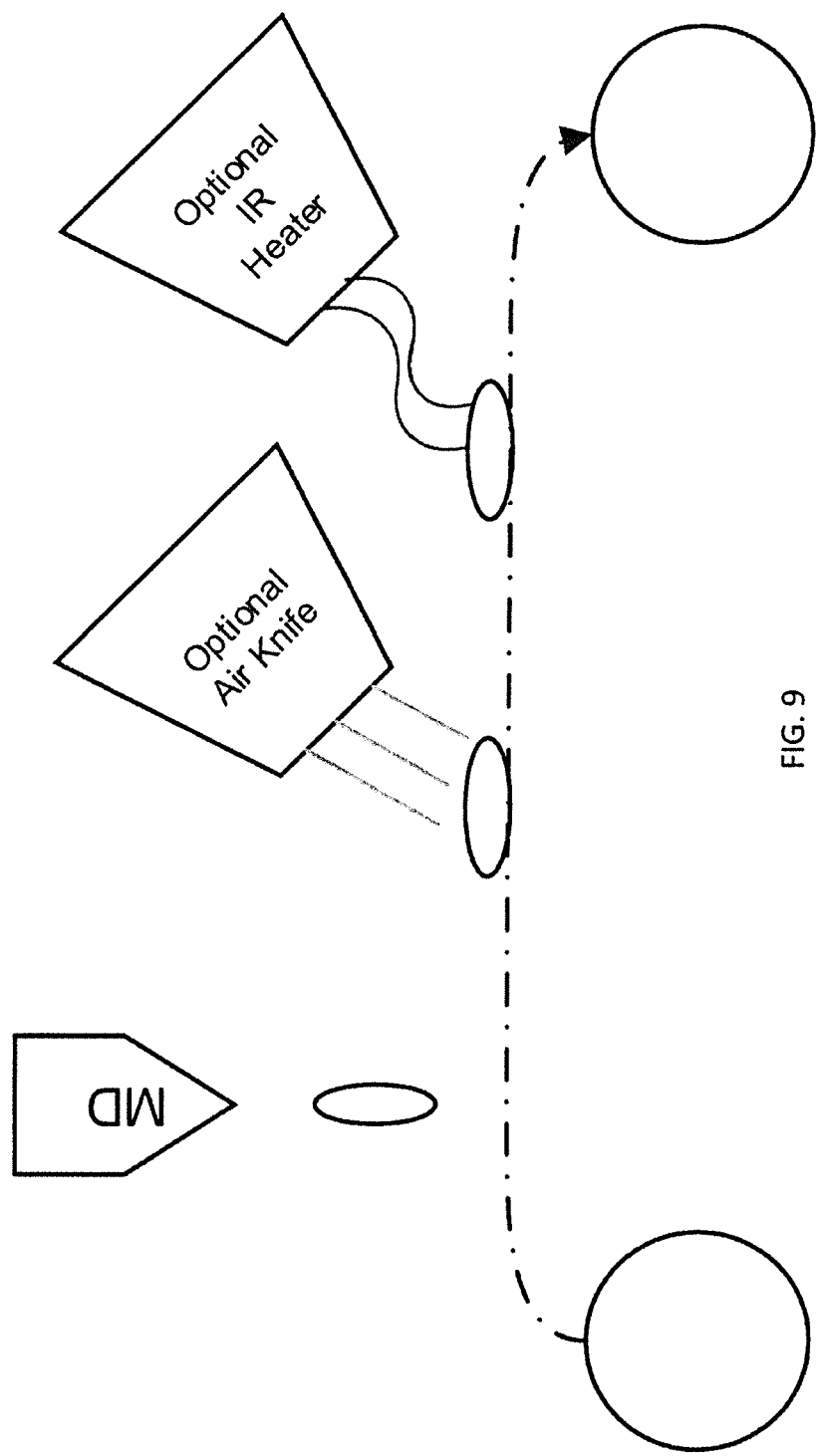
FIG. 9 schematically illustrates deposition onto the muco-adhesive substrate using positive displacement through a narrow tip.
Figure 10:
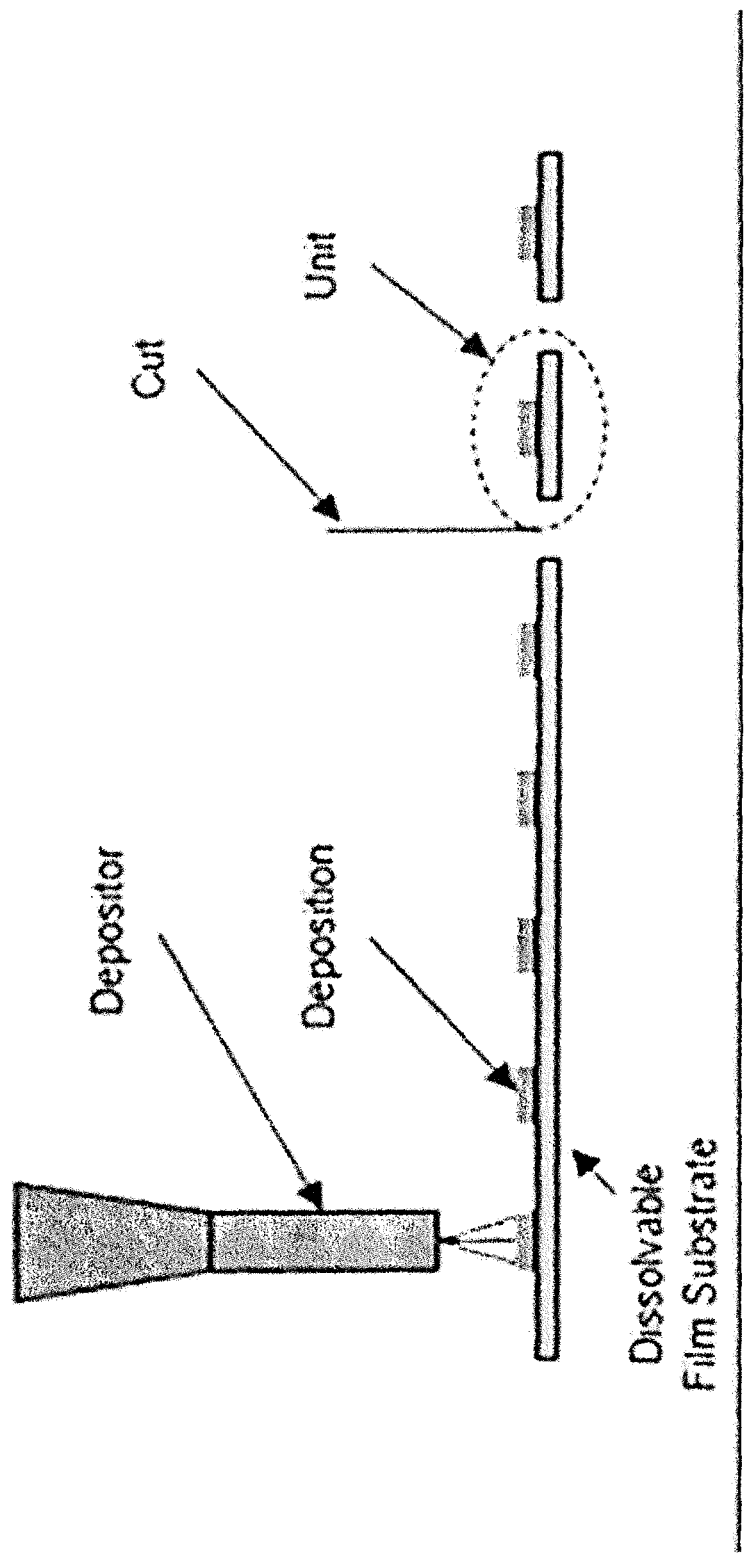
FIG. 10 schematically illustrates deposition onto the muco-adhesive substrate using a jetting system.

FIG. 1 illustrates an exemplary system for carrying out the direct dispensing in which a depositor 100 containing a dispenser head of the type described herein dispenses the dissolvable compositions including active ingredients directly onto muco-adhesive substrates 20 to form dissolvable unit dose film constructs 10. For example, FIGS. 9 and 10 schematically illustrate the use of a dispenser head having a narrow tip for dispensing the volume by a piezoelectric actuator and having a controllable valve for jetting onto the muco-adhesive substrate, respectively. The muco-adhesive substrate 20 may emerge from a depositor 100 along a conveyor 200.

Once the dissolvable composition has been deposited on the muco-adhesive substrate 20 or other surface on which it is deposited, the solvent (e.g., water) may be removed by a thermal drying process to leave the dissolvable unit dose film construct 10 in a form that is self-supporting and may subsequently be applied. Any suitable drying process may be employed, including forced ambient air, chilled air, and inert gases. Exemplary methods include, but are not limited to, gas-forced air drying in which hot air is blown down on the deposit at high velocity to minimize the boundary layer and facilitate mass transfer, drying in a box oven, IR drying, and combinations thereof. Alternatively, nitrogen or argon gas may be blown down on the deposit. In some embodiments, the combination of small volumes and the use of a high volatility pharmaceutically acceptable solvent (such as ethanol, acetone, and the like) reduce drying times, which can in turn assist, for example, in applying active layers on opposing sides of the muco-adhesive substrate 20 as described with respect to FIGS. 4a and 4b, which can be flipped quickly after initial deposition to form the active layers on the substrate.

In one embodiment, individual thin film unit doses are direct dispensed in an array on a stationary but continuous web of polymer film as the substrate 20 as described with respect to FIG. 1. Following deposition of that array by direct dispensing, the web is advanced a predetermined distance upon which another array is then formed by direct dispensing on the web at a different location. While the second array is being deposited, a vacuum encapsulation fixture is lowered over the first array using the polymer film as the base of the enclosure within which vacuum is applied. Some heat may also be applied if needed or desired. After deposition of the second array and drying of the first, the vacuum is relieved and the encapsulation fixture is raised or removed. The web is advanced and the process proceeds in a step-and-repeat manner, with the second array subjected to vacuum drying with the encapsulation fixture while a third array is direct dispensed.

It will be appreciated that the polymer film may be held in place during the encapsulation process to reinforce it against collapse when the vacuum is applied. For example, application of a vacuum may be applied to the opposite, underlying side of the film (i.e., opposite from that on which the active formulation was deposited). The resulting applied suction may be accomplished, for example, using an array of holes in a flat metal plate and firmly holds the film in place prior to positioning of the vacuum fixture and vacuum application.

In addition to improvements to the manufacture of thin films, the use of direct dispensing to deposit discrete amounts of active formulation may also provide an ability to achieve improvements in the construction of the films thereby formed.

Some conventional drug delivery films employ a two-layer design in which a first layer contains a formulation containing the active ingredient and a second layer serves as an inactive backing layer or a layer containing a different active ingredient or the same active ingredient at a different concentration. The second or backing layer may be the same or a different formulation as the first layer, except that it does not otherwise contain the same active ingredient or same level of active ingredient found in the first layer. The backing layer may serve as a barrier against flow of the active ingredient, for example, into the oral cavity and the gastrointestinal tract. A significant drawback to conventional films and their related wide web production processes is that they require the first and second layers to be of the same area. The layers are formed as overlying webs in which one of the layers is coated via a second, separate casting or laminating step on top of the other layer. In addition to requiring first and second layers of the same area, this process also still results in a master roll that requires slitting into narrower width rolls coupled with removal of the beginning and end of the rolls to achieve defect-free slit rolls of uniform coated layer thickness. These same considerations apply to situations calling for more than two layers.

Figures 2, 3:
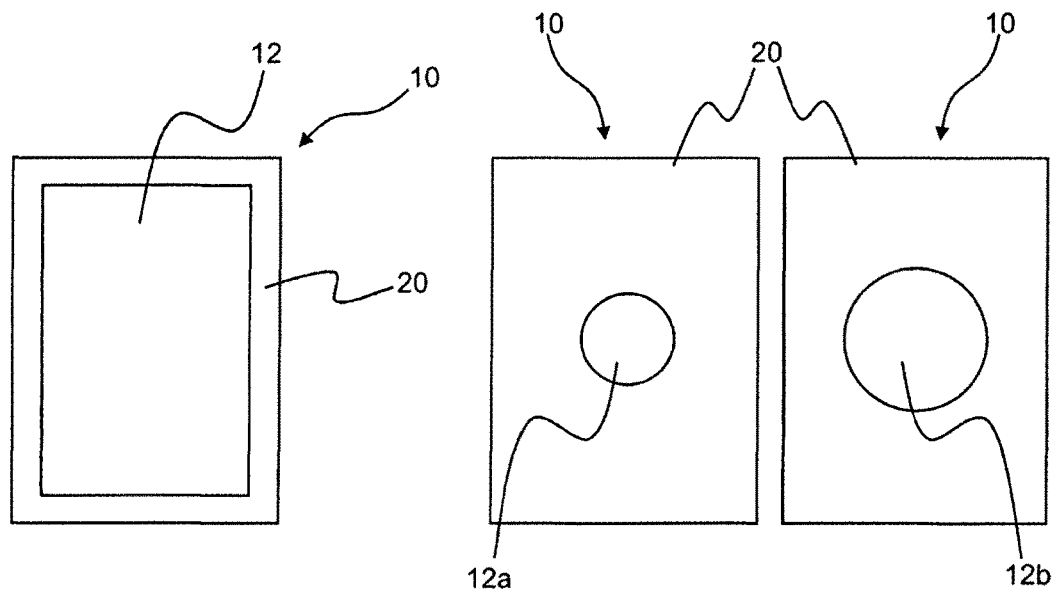
FIG. 2 illustrates a dissolvable unit dose film construct having a window frame effect, according to an embodiment of the present disclosure.
FIG. 3 illustrates dissolvable unit dose film constructs having differing sizes of dissolvable active layers, according to an embodiment of the present disclosure.

Present embodiments employing unit dose deposition by direct dispensing may overcome these drawbacks by providing a two-layer film that includes direct dispensing a smaller area of the active layer within a larger area defined by the backing layer. This may be used to create a window frame effect as shown in FIG. 2, in which the dissolvable unit dose film construct 10 is a multi-layer film containing a muco-adhesive substrate 20 and a smaller, first dissolvable active layer 12. The muco-adhesive substrate 20 thus provides a peripheral seal around the first dissolvable active layer 12 when dissolvable unit dose film construct 10 is applied to mucosa. This may prevent leakage of the active ingredient from the periphery of the first dissolvable active layer 12 into the oral cavity and may further increase the likelihood that all of the drug or other active ingredient is delivered via the desired mucosal pathway.

In addition, the use of the window frame may be used to effectively seal the first dissolvable active layer 12 and thereby mask an offensive taste due to the active ingredient. The muco-adhesive substrate 20 may prevent leakage of the drug from the first dissolvable active layer 12 into the oral cavity where perceptible taste would occur.

A further advantage of present embodiments over conventional two-layer films is that by direct dispensing the first dissolvable active layer 12 in discrete unit doses onto the muco-adhesive substrate 20, enhanced dose accuracy and uniformity between dissolvable unit dose film constructs 10 may be achieved because a consistent, precise volume of the dissolvable compositions is applied independent of area or thickness of the backing layer. Temperature control of the dispensed fluid and temperature control of the jetting system actuator may provide repeatability of dispensed doses. Conversely, in conventional wide web film manufacture, deposition thickness characterization is typically accomplished by characterizing the weight deposited per unit area (i.e., "coating weight" sampling). While process parameters are typically adjusted at the front end of a coating campaign and then maintained after the desired target is achieved, the precision of the coating weight of the active layer is affected by variability in the thickness of the underlying backing layer. For example, a depression in or thinning of the backing layer would result in a localized area of greater thickness of the active layer. This concern may be overcome in certain of the present embodiments because each dissolvable active layer 12 may be individually measured and dispensed as a consistent volume regardless of any variation in the muco-adhesive substrate 20 to which it is applied. It will further be appreciated that exemplary embodiments may also be used to deposit discrete active layers onto a backing layer that is a continuous web, although that would have the effect of re-introducing certain trimming and other conversion steps in manufacturing. However, the active ingredient loss is expected to be much less for units produced by deposition of the active ingredient-containing formulation onto an inactive backing layer because the trimmed material will not contain the expensive active ingredient.

Referring to FIG. 3, in certain embodiments different dosage strengths may be achieved by forming smaller or larger first dissolvable active layers 12 on the muco-adhesive substrates 20. Thus, the same size muco-adhesive substrate 20 may be used to deliver the same size film across multiple dosage strengths. Likewise, the same size first dissolvable active layer 12 may be used with different sized muco-adhesive substrates 20 modifiable to meet a particular class of users' ability to handle the dissolvable unit dose film construct 10, which may be independent of the amount of active ingredient to be delivered (i.e., larger films may be desired for pediatric or geriatric patients). This may also be of particular benefit for low dosage and/or particularly potent drugs which, if used alone without a backing layer, might require a unit dose area so small that the resulting film would otherwise be too difficult to handle.

As shown in FIG. 3, two dissolvable unit dose film constructs 10 may be formed with a uniformly sized muco-adhesive substrate 20. In the first dissolvable unit dose film construct 10, a small dissolvable active layer 12a is deposited to the muco-adhesive substrate 20, for example, for use in a pediatric size dose of the active ingredient that still provides a dissolvable unit dose film construct 10 that, by virtue of the size of the muco-adhesive substrate 20, is large enough to be easily handled. For an adult size dose, that same muco-adhesive substrate 20 may be used with a larger dissolvable active layer 12b deposited thereon to deliver a larger amount of the active ingredient, with the same size dissolvable unit dose film construct 10. Because the area of the first dissolvable active layer 12 is adjustable by deposit volume, the same active formulation may be used for both the pediatric and the adult dose.

An additional benefit achieved by exemplary embodiments that use the same size muco-adhesive substrate 20 for small and large dissolvable active layers 12a, 12b of different size is standardization of the overall film size across multiple dosage strengths. As a result, tooling and packaging may also be standardized with respect to the same overall film size defined by the area of the muco-adhesive substrate 20.

It will be appreciated that in some embodiments, it may be desirable to incorporate additional ingredients into the active layer formulations used to produce small and large dissolvable active layers 12a, 12b of different dosage strengths to more easily differentiate between them, particularly because the overall size of the doses containing small and large dissolvable active layers 12a, 12b may be visually similar. Differentiation may be achieved, for example, by the use of different colors for active layers of different strengths. Colorants may also be used to distinguish dissolvable unit dose film constructs 10 having different active ingredients, even if the size or strength of the dosage is the same. Colorants also provide visual recognition to a vision system that measures the surface area of the dispensed feature and applies pass/fail criteria based upon a software algorithm associated with the vision system camera.

In some cases, two active ingredients must be conveyed to a recipient at the same time. This may be achieved by combining two different active ingredients in the active-layer formulation. However, that combination may not be possible in many circumstances, such as, for example, where the active ingredients are incompatible (e.g., they react or degrade when in contact with one another). Alternatively, two different pH buffers may be required, each active ingredient requiring a different buffering system to affect solubility or to improve bioavailability. However, it is not possible to incorporate two different buffers in the same formulation to yield two different pH values.

Figures 4A, 4B, 5:
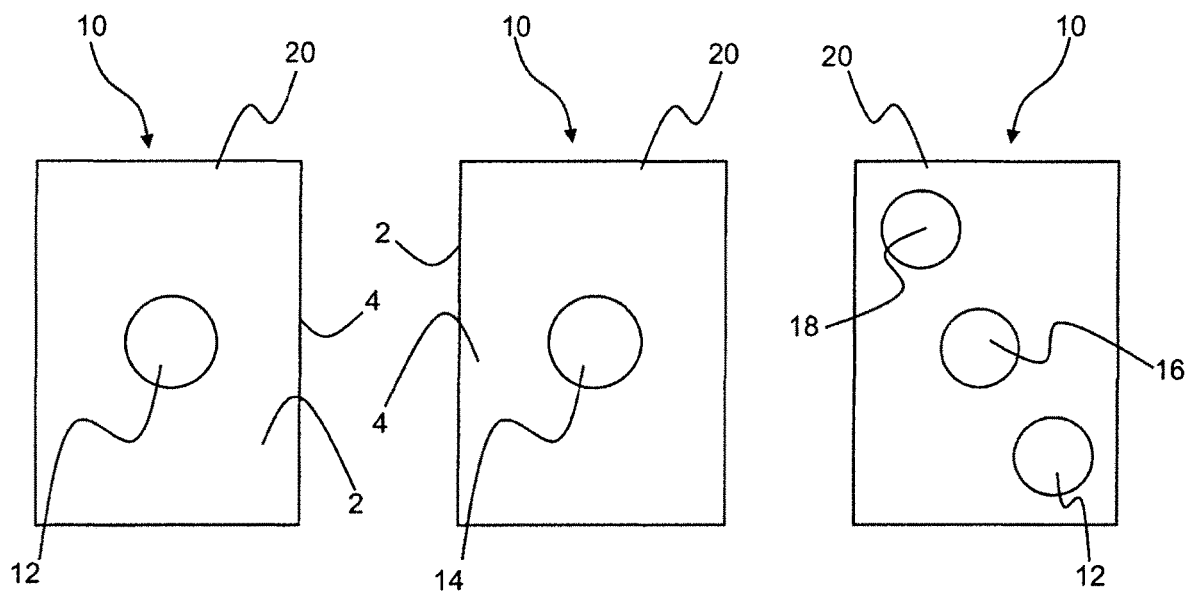
FIG. 4a illustrates a dissolvable unit dose film construct having a first dissolvable active layer on a first side of a muco-adhesive substrate, according to an embodiment of the present disclosure.
FIG. 4b illustrates the dissolvable unit dose film construct of FIG. 4a having a second dissolvable active layer on a second side of the muco-adhesive substrate, according to an embodiment of the present disclosure.
FIG. 5 illustrates a dissolvable unit dose film construct having a plurality of discrete active layers in a muco-adhesive substrate, according to an embodiment of the present disclosure.

As shown in FIGS. 4a and 4b, a dissolvable unit dose film construct 10 may be formed with a first dissolvable active layer 12 formed on a first side 2 of a muco-adhesive substrate 20 (FIG. 4a), and a second dissolvable active layer 14 formed on a second side 4 of the muco-adhesive substrate 20 (FIG. 4b). The first dissolvable active layer 12 and the second dissolvable active layer 14 may have the same composition or different compositions, the same active ingredient or different active ingredients, the same size/dosage or different sizes/dosages, or different combinations thereof.

In this embodiment, after the first active layer 12 is applied to the substrate 20, the substrate can be flipped for applying the second active layer 14 as a second dissolvable composition comprising a polymer matrix, the polymer matrix comprising a water-soluble polymer, a water-dispersible polymer, a water-swellable polymer, or combinations thereof, the second dissolvable composition further comprising an active ingredient and a liquid carrier. The second dissolvable composition is deposited onto the muco-adhesive substrate 20 as a plurality of individual dosage units on an opposing side (second side 4 as opposed to the first side 2) of the muco-adhesive substrate 20 from the first dissolvable composition. The individual dosage units are dried to remove at least a portion of the liquid carrier from the second dissolvable composition, forming the second dissolvable active layer 14. The active ingredient of the second dissolvable composition may be the same as the active ingredient of the first dissolvable composition, or the active ingredient of the second dissolvable composition may be compositionally distinct from the active ingredient of the first dissolvable composition.

In yet another embodiment, as shown in FIG. 5, the method of forming the dissolvable unit dose film construct 10 includes depositing the second dissolvable composition onto the muco-adhesive substrate 20 as a plurality of individual dosage units spatially isolated from the first dissolvable composition. At least a portion of the liquid carrier is removed from the second dissolvable composition, forming a second dissolvable active layer 16 on the same side of the muco-adhesive substrate 20 as the first dissolvable active layer 12.

In a further embodiment, the method of forming the dissolvable unit dose film construct 10 includes forming a third dissolvable composition comprising a polymer matrix, the polymer matrix comprising a water-soluble polymer, a water-dispersible polymer, a water-swellable polymer, or combinations thereof, the third dissolvable composition further comprising an active ingredient and a liquid carrier. The third dissolvable composition is deposited onto the muco-adhesive substrate 20 as a plurality of individual volumes spatially isolated from the first dissolvable composition and the second dissolvable composition. The individual dosage units are dried to remove at least a portion of the liquid carrier from the third dissolvable composition, forming a third dissolvable active layer. The active ingredient of the third dissolvable composition may be the same as the active ingredient of the first dissolvable composition, the second dissolvable composition, or both, or the active ingredient of the third dissolvable composition may be compositionally distinct from the active ingredient of the first dissolvable composition, the second dissolvable composition, or both, forming a third compositionally distinct dissolvable active layer 18. Any suitable number of additional dissolvable compositions may be formed and deposited in the same manner to generate any suitable number of additional dissolvable active layers.

In another embodiment, a method for forming a dissolvable unit dose film construct 10 includes providing a muco-adhesive composition including a polymer matrix, wherein the polymer matrix includes a water-soluble polymer, a water-dispersible polymer, a water-swellable polymer, or combinations thereof, and a liquid carrier. The muco-adhesive composition is dried to remove at least a portion of the liquid carrier, forming a muco-adhesive substrate 20. A first dissolvable composition is formed including a polymer matrix, wherein the polymer matrix includes a water-soluble polymer, a water-dispersible polymer, a water-swellable polymer, or combinations thereof, an active ingredient, and a liquid carrier. The first dissolvable composition is deposited onto the muco-adhesive substrate 20 as a plurality of individual dosage units and the plurality of individual dosage units is maintained without further active drying such that plurality of individual dosage units is a plurality of first dissolvable active layers 12. The muco-adhesive composition may further include an active ingredient. The active ingredient of the muco-adhesive composition may be the same as the active ingredient of the first dissolvable composition or may be compositionally distinct from the active ingredient of the first dissolvable composition.

Any suitable combination of a muco-adhesive substrate 20 with any suitable number of dissolvable active layers disposed on the first side 2 or the second side 4 may be formed by appropriate combinations of the foregoing embodiments, including with any suitable number of active ingredients imbued in any suitable combination and distribution within the muco-adhesive substrate 20 and the dissolvable active layers.

The muco-adhesive substrate 20 may be formed as a continuous web of film, followed by dividing the muco-adhesive substrate 20 into smaller individual films after the formation of the dissolvable unit dose film constructs 10.

The dissolvable compositions may be characterized broadly as liquid-base biologically compatible film-forming polymer matrices, optionally containing an active ingredient, which form erodible, disintegrable and/or dissolvable films upon drying, and which may include, without limitation, the dissolvable compositions described in U.S. Pat. No. 7,470,397 to Meathrel et al., which is incorporated by reference in its entirety as if fully-restated herein. It will be appreciated that the resulting films have a combination of a solid content sufficient to provide film strength to aid in handling but balanced to provide disintegration at a predetermined rate. The dissolvable compositions may be further characterized broadly as liquid-base biologically compatible film-forming polymer matrices containing a high concentration of an active ingredient, which forms an active-containing layer upon drying.

Any suitable polymers may be employed as the polymer matrices. It will be appreciated that the polymer or polymers selected for any particular embodiment may depend on a variety of factors, including the active ingredient or active ingredients to be incorporated or deposited, the desired rate of disintegration (which may be modified with or without the use of a surfactant), and the rheology of the liquid formulation used to form the muco-adhesive substrates 20 or the dissolvable active layers, as well as other factors known to those of ordinary skill in the art for producing conventional thin film constructs.

The polymer or polymers may be water-soluble, water-dispersible, water-swellable, water-insoluble, or combinations thereof, and may include cellulose or cellulose derivatives. Although the use of water-swellable and water-insoluble polymers is contemplated, the formulations will include a sufficient amount of water-soluble polymer and/or water-dispersible polymer to ensure the eventual disintegration of the subsequently formed film.

Exemplary polymers include, but are not limited to, water-soluble hydroxypropylmethyl cellulose, hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, polyethylene oxide, chitosan, xanthan gum, tragacantha, guar gum, acacia gum, arabic gum, carrageenan, pululan, polyacrylic acid, methylmethacrylate copolymer, carboxyvinyl copolymers, and various copolymer or combinations of the above and other known water-soluble polymers, cellulose derivatives, and/or gums, among others. Other polymers that may be used include, but are not limited to, ethyl cellulose, hydroxypropyl ethyl cellulose, cellulose acetate phthalate, hydroxypropyl methyl cellulose phthalate, copolymers thereof, and combinations thereof.

In some embodiments, the polymer matrix may include a surfactant to adjust the rate of dissolution. In other embodiments, the rate of dissolution may be adjusted by the use of a combination of high and low molecular weight polymers with or without the use of a surfactant. For example, particularly beneficial properties of film strength and disintegration profile (i.e., the rate at which a film disintegrates upon contact with the oral cavity or other mucosa) are obtained when the water soluble components include a combination of low molecular weight polymers (e.g., those less than about 5 kDa to 60 kDa) and high molecular weight polymers (e.g., those of greater than 60 kDa to about 150 kDa, up to about 900 kDa, or higher).

Various other polymers may be selected by one of ordinary skill in the art given the teachings herein and preferably include a sufficient amount of a high molecular weight component to impart adequate film strength and a sufficient amount of a low molecular weight component to facilitate the desired film property of the disintegration profile. Additionally, one may select a single water-soluble polymer as the film matrix-forming ingredient with other ingredients that assist with film strength and disintegration, such as surfactants, fillers, and plasticizers. It will further be appreciated that other constituents useful in processing the film may be employed, including rheology modifiers. Any suitable modifiers may be used including acrylic polymer potassium salts, such as acrylic acid polymer crosslinked with divinyl glycol (commercially available as NOVEON by Lubrizol). The choice of any particular inactive formulation ingredient combination may also be dependent, in part, on its interaction with the active ingredient or ingredients and its influence on the properties of the active ingredient or ingredients.

The water-soluble low molecular weight component need not be a water-soluble polymer. Instead, the low molecular weight component may be other low molecular weight molecules, monomers, oligomers or a combination thereof (e.g., xylitol, glycerol, polyethylene glycol, propylene glycol). The low molecular weight component may serve to promote disintegration but is present in an amount such that film strength is adequate for processing and dispensing. Various concentrations of the low molecular weight component may be utilized.

The amounts of high and low molecular weight components may be adjusted to achieve a desired disintegration profile, which may range from a few seconds to several minutes or even hours. When slower disintegration is desired, the concentration of the high molecular weight component may be increased relative to the concentration of the low molecular weight component. When faster disintegration is desired, the concentration of the low molecular weight component may be increased relative to the concentration of the high molecular weight component. Additionally, the thickness of the dissolvable unit dose film construct 10 may be adjusted to achieve a desired disintegration profile. To increase the disintegration time, the thickness is increased. Adequate film strength should be maintained to allow for handling of the film.

In addition to any active ingredient, other ingredients that may be incorporated may include, but are not limited to, a plasticizer, sweetener, thickener, buffer, stabilizer, flavorings, and/or other additives and which are preferably, but not necessarily, water-soluble. The types and amounts of such ingredients are familiar to those within the art for formulating conventional dissolvable thin films. It will be appreciated, however, that exemplary embodiments, which employ deposition of individual, discrete unit doses, may have an overall solid or non-volatile content in the formulation that is less than that used in conventional methods but significantly lower volumes are deposited and, as a result, require less drying time, if any drying time whatsoever. Thus, while referred to herein as a liquid formulation that is employed to form the individual unit dose films, it will be appreciated that term encompasses any wet, non-solid flowable substance. In some embodiments, a buffer is introduced into the formulation for the muco-adhesive substrate 20 and not in the formulation(s) of the one or more active layers. In other embodiments, a buffer is introduced into the formulation(s) for the one or more active layers but not the formulation for the muco-adhesive substrate 20. In still other embodiments, a buffer is employed in formulations for both the muco-adhesive substrate 20 and the active layer(s), while in others, no buffer is employed. In some embodiments, neotame and/or sucralose may be employed as sweeteners. It will further be appreciated that in some embodiments the additives in the compositions for the active layer may also be used to separate ingredients from those which are found in the substrate. For example, a sweetener or other ingredient that is incompatible with the active ingredient (for example, which may cause precipitation of the active) used to form the active layer may instead by incorporated into the composition used to form the muco-adhesive substrate 20.

Dissolvable unit dose film constructs 10 may include one or more active ingredients, typically, but not necessarily, a pharmaceutical drug. A wide range of active ingredients may be incorporated into the polymer matrix or applied onto the polymer matrix. The active ingredient may be deposited prior to or following film formation and may be incorporated in any form, including as a solution, emulsion, suspension, or dispersion. The specific form may depend upon the particular combination of active ingredient and polymer to be employed. That is, active ingredient-containing liquid formulations that are deposited onto the films may be in the form of a solution in which all ingredients, including any drug substances, are fully dissolved and soluble in the bulk liquid; as an emulsion, typically used for aqueous formulations to which an oil-soluble ingredient, such as a flavoring, has been added; and suspensions or dispersions in which insoluble active ingredients or other excipients may be added to the bulk-liquid formulation while still achieving uniformity of distribution in the subsequently deposited layer and formed dissolvable unit dose film construct 10.

Active ingredients may include, but are not limited to, ace-inhibitors, antianginal drugs, anti-arrhythmias, anti-asthmatics, anti-cholesterolemics, anxiolytics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-Parkinson agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof. The types and amounts of active ingredients to be employed are familiar to those within the art for formulating conventional dissolvable thin films.

In some embodiments, the active ingredient comprises buprenorphine. If a sweetener is used in compositions containing buprenorphine.

Embodiments are further described and illustrated with respect to the following examples, which are presented by way of explanation, not of limitation.

EXAMPLES

Example 1

Ingredients were combined and mixed together by vortexing on a suitable mixer to form a homogeneous fluid according to Table 1.

TABLE 1

| Ingredient | Amount |
| --- | --- |
| Hydroxypropyl cellulose (M.W. about 34 kDa) | 2.891 g |
| Acetone | 23.343 g |
| Apomorphine HCl hemihydrate | 4.804 g |

Example 2

154 µL of the formulation of Example 1 was microdeposited onto the surface of a 22 mm×22 mm die-cut film composed of sodium carboxymethyl cellulose and phosphate buffer to yield an equivalent of 23 mg apomorphine HCl hemihydrate for each unit dose film.

Example 3

Ingredients were blended together on an overhead stirrer to form a solution according to Table 2.

TABLE 2

| Ingredient | Liquid Mix Concentration (wt %) | Dry Film Concentration (wt %) |
| --- | --- | --- |
| Ethanol | 63.73 | — |
| Water | 11.26 | — |
| Vardenafil Base | 3.58 | 14.31 |
| Hydroxypropylcellulose M.W. about 80 kDa | 9.64 | 38.53 |
| Hydroxypropylcellulose (M.W. about 77 kDa) | 9.64 | 38.53 |
| Hydroxypropylcellulose M.W. about 34 kDa | 2.16 | 8.63 |
| TOTAL | 100.00 | 100.00 |

A monolithic film was produced by coating the liquid of Example 3 onto a polyester substrate and drying the wet film in a laboratory convection oven for 40 minutes at 70° C. The dry film weight measured 70 mg per 422.4 mm$^2$ and contained 0.024 mg vardenafil free base per mm$^2$. Units were die-cut to 23.6 mm$^2$ to be used in diffusion studies and contained 0.56 mg vardenafil base.

Example 4

Ingredients were blended together on an overhead stirrer to form a solution according to Table 3.

TABLE 3

| Ingredient | Liquid Mix Concentration (wt %) | Dry Film Concentration (wt %) |
| --- | --- | --- |
| Water | 82.00 | — |
| Hydroxyethylcellulose (M.W. about 90 kDa) | 18.00 | 100.00 |
| TOTAL | 100.00 | 100.00 |

A film was produced by coating the liquid of Example 4 onto a polyester substrate and drying the wet film in a laboratory convection oven for 50 minutes at 70° C. The dry film weight measured 55 mg per 422.4 mm$^2$.

Example 5

Ingredients were blended together on an overhead stirrer to form a solution according to Table 4.

TABLE 4

| Ingredient | Liquid Mix Concentration (wt %) | Theoretical Dry Deposit Concentration (wt %) |
|---|---|---|
| Ethanol | 67.99 | — |
| Water | 12.01 | — |
| Vardenafil Free Base | 2.86 | 14.29 |
| Hydroxypropylcellulose (M.W. about 80 kDa) | 7.71 | 38.53 |
| Hydroxypropylcellulose (M.W. about 77 kDa) | 7.71 | 38.53 |
| Hydroxypropylcellulose (M.W. about 34 kDa) | 1.73 | 8.65 |
| TOTAL | 100.00 | 100.00 |

22 µL of Example 5 solution was microdeposited onto the dried film of Example 4 with a positive displacement pipette. The dispensed liquid was dried in a laboratory convection oven for 30 minutes at 70° C. The surface area of the dried microdeposition was 12.56 mm$^2$ and contained 0.559 mg vardenafil free base. All units were die-cut to 52.65 mm$^2$ and encompassed the 12.56 mm$^2$ active deposition.

Example 6

Figure 6:
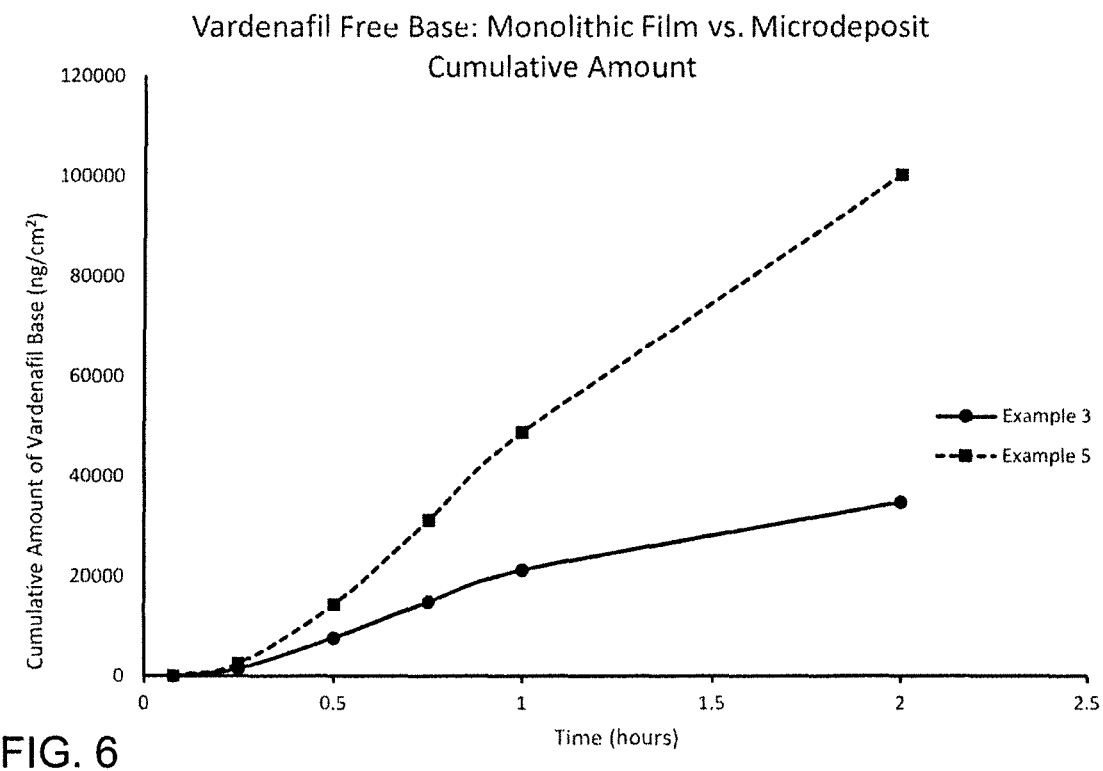
FIG. 6 is a graph of cumulative vardenafil concentrations plotted with respect to time, according to a comparison of examples.

A diffusion study was conducted comparing the permeability of the 23.6 mm$^2$ units of Example 3 to the 52.65 mm$^2$ units of Example 5. ORL-200 24-well plate (MatTek Corp., Ashland, MA) containing oral cell tissue cultures were utilized as the diffusion membrane. The tissues were equilibrated in a 5% $CO_2$ chamber set to 37° C. and 95% relative humidity. 300 µL of Dulbecco's Phosphate Buffered Saline (DPBS) receiver media was added to each well within the 24-well plate and placed into the $CO_2$ chamber overnight. The following morning the tissue inserts were removed from the ORL-200-ASY assay medium and transepitheleal electrical resistance (TEER) was measured on each tissue insert to assure viability following the overnight equilibration. The tissues were then placed into a 24-well plate containing 300 µL of pre-equilibrated DPBS receiver media. Each insert was pre-wetted with 25 µL of DPBS prior to applying the respective Example film to the donor side of the tissue insert, followed by an additional 25 µL of DPBS onto the top of each prototype. The 24-well plate containing each tissue insert was returned to the incubator for the specified time frame and subsequently removed from the incubator following the elapsed time. The tissue inserts were transferred to a fresh 24-well plate containing 300 µL of receiver media and returned to the incubator for the additional specified time. 300 µL of receiver media from each well of the 24-well plate was transferred to an HPLC vial and analyzed via UPLC. This experimental sequence was repeated for all time points (i.e. 5, 15, 30, 45, 60, and 120 minutes). As shown in FIG. 6, the cumulative vardenafil concentrations are plotted with respect to time. When normalized to active surface area, the microdeposited prototype Example 5 outperformed the monolithic prototype Example 3, as delineated in the table of cumulative vardenafil concentration (ng/cm$^2$/h).

| Average Cumulative Amount (ng/cm$^2$) | | |
|---|---|---|
| Time | Example 3 | Example 5 |
| 1 h | 21,198 | 48,677 |

Example 7

Ingredients were blended together on an overhead stirrer to form a solution according to Table 5.

TABLE 5

| Ingredient | Liquid Mix Concentration (wt %) | Dry Film Concentration (wt %) |
|---|---|---|
| Ethanol | 56.25 | — |
| Water | 18.75 | — |
| Buprenorphine HCl | 4.32 | 17.28 |
| Hydroxypropylcellulose (M.W. about 80 kDa) | 9.30 | 37.20 |
| Hydroxypropylcellulose (M.W. about 77 kDa) | 9.30 | 37.20 |
| Hydroxypropylcellulose (M.W. about 34 kDa) | 2.08 | 8.32 |
| TOTAL | 100.00 | 100.00 |

A monolithic film was produced by coating the liquid of Example 7 onto a polyester substrate and drying the wet film in a laboratory convection oven for 30 minutes at 40° C. followed by 15 minutes at 70° C. The dry film weight measured 50 mg per 281.6 mm$^2$ and contained 0.031 mg buprenorphine HCl/mm$^2$. Units were die-cut to 26.4 mm$^2$ to be used in diffusion studies and contained 0.81 mg buprenorphine HCl.

Example 8

Ingredients were blended together on an overhead stirrer to form a solution according to Table 6.

TABLE 6

| Ingredient | Liquid Mix Concentration (wt %) | Theoretical Dry Deposit Concentration (wt %) |
|---|---|---|
| Ethanol | 63.75 | — |
| Water | 21.25 | — |
| Buprenorphine HCl | 4.50 | 30.00 |
| Hydroxypropylcellulose (M.W. about 80 kDa) | 4.72 | 31.47 |
| Hydroxypropylcellulose (M.W. about 77 kDa) | 4.72 | 31.47 |
| Hydroxypropylcellulose (M.W. about 34 kDa) | 1.06 | 7.06 |
| TOTAL | 100.00 | 100.00 |

Viscosity of the resulting solution from Example 8 was measured on a Brookfield DV-2T LV viscometer at 25° C. using spindle SC4-27 and a shear rate of 1.02 sec$^{-1}$. The resulting viscosity was 602 cps. 24 µL of Example 8 solution was microdeposited onto the dried film of Example 4 with a positive displacement pipette. The dispensed liquid was dried in a laboratory convection oven for 30 minutes at 70° C. The surface area of the dried microdeposition was 12.56 mm$^2$ and contained 0.813 mg buprenorphine HCl. All units were die-cut to 52.65 mm$^2$ and encompassed the 12.56 mm$^2$ active deposition.

Example 9

Figure 7:
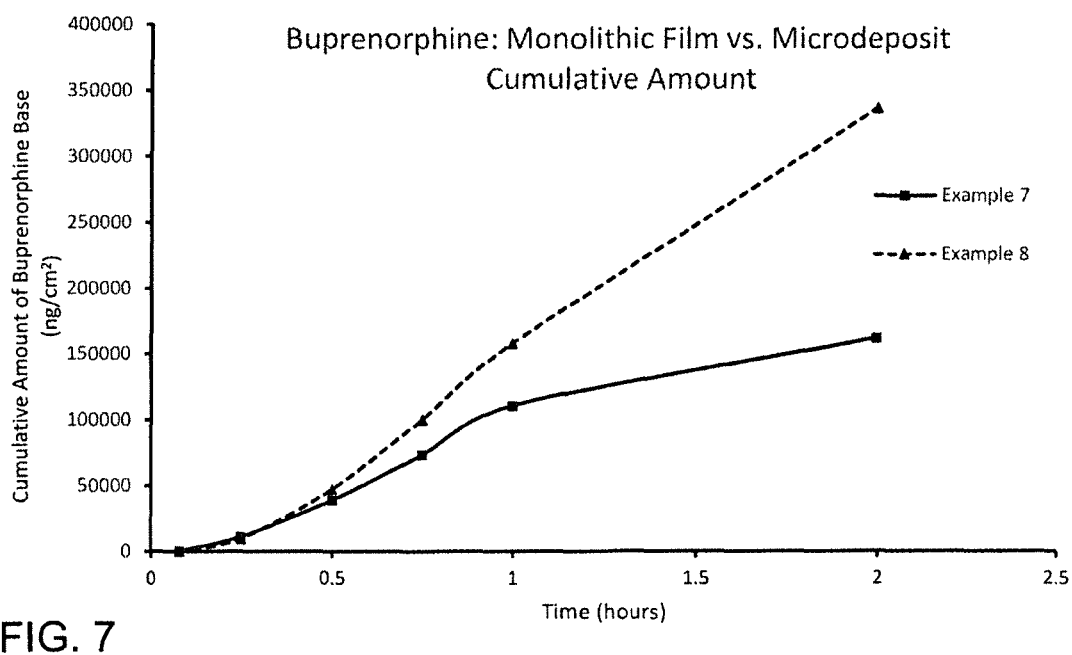
FIG. 7 is a graph of cumulative buprenorphine concentrations plotted with respect to time, according to a comparison of examples.

A diffusion study was conducted comparing the permeability of the 26.4 mm$^2$ units of Example 7 to the 52.65 mm$^2$ units of Example 8. The permeability procedure from Example 6 was followed. As shown in FIG. 7, the cumulative buprenorphine concentrations are plotted with respect to time. When normalized to surface area, the microdeposited prototype Example 8 outperformed the monolithic prototype Example 7, as delineated in the table of cumulative buprenorphine concentration (ng/cm²/h).

| Average Cumulative Amount (ng/cm²) | | |
|---|---|---|
| Time | Example 8 | Example 7 |
| 1 h | 157,930 | 110,653 |

Example 10

Ingredients were blended together on an overhead stirrer to form a solution according to Table 7.

TABLE 7

| Ingredient | Liquid Mix Concentration (wt %) | Dry Film Concentration (wt %) |
|---|---|---|
| Water | 82.00 | — |
| Hydroxyethylcellulose (M.W. about 90 kDa) | 16.78 | 93.22 |
| Sodium Acetate, anhydrous | 1.17 | 6.50 |
| Acetic Acid | 0.05 | 0.28 |
| TOTAL | 100.00 | 100.00 |

A film was produced by coating the liquid of Example 10 onto a polyester substrate and drying the wet film in a laboratory convection oven for 50 minutes at 70° C. The dry film weight measured 55 mg per 422.4 mm².

Example 11

24 µL of Example 8 solution was microdeposited onto the dried film of Example 10 with a positive displacement pipette. The dispensed liquid was dried in a laboratory convection oven for 30 minutes at 70° C. The surface area of the dried microdeposition was 12.56 mm² and contained 0.813 mg buprenorphine HCl. All units were die-cut to 52.65 mm² and encompassed the 12.56 mm² active deposition.

Example 12

Figure 8:
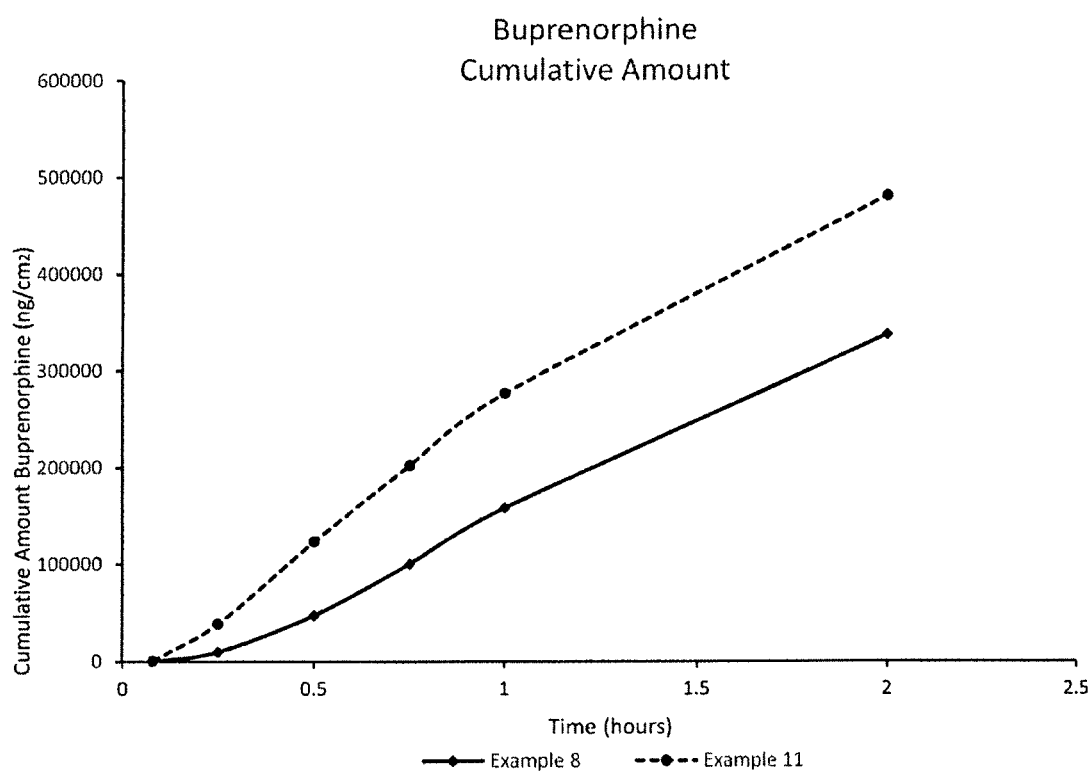
FIG. 8 is a graph of cumulative buprenorphine concentrations plotted with respect to time, according to a comparison of examples.

A diffusion study was conducted comparing the permeability of the 52.65 mm² units of Example 11 to the 52.65 mm² units of Example 8. The permeability procedure from Example 6 was followed. As shown in FIG. 8, the cumulative buprenorphine concentrations are plotted with respect to time. When normalized to surface area, the microdeposited prototype Example 11 outperformed the microdeposited prototype Example 8, as delineated in the table of cumulative buprenorphine concentration (ng/cm²/h), with Example 12—in which the substrate film contained a buffer—provided additional benefit with respect to drug diffusion.

| Average Cumulative Amount (ng/cm²) | | |
|---|---|---|
| Time | Example 11 | Example 8 |
| 1 h | 276,411 | 157,930 |

The above description is only illustrative of the preferred embodiments which achieve the objects, features and advantages of the present invention. It is not intended that the present invention be limited to the illustrated embodiments.

Example 13

Ingredients were blended together on an overhead stirrer to form a solution according to Table 8.

TABLE 8

| Example | Excipient | Liquid Mix Concentration (wt %) | Dry Film Concentration (wt %) |
|---|---|---|---|
| 13 | Water | 82.00 | — |
| | Hydroxyethylcellulose (M.W. about 90 kDa) | 16.24 | 90.22 |
| | Sodium Acetate, anhydrous | 1.17 | 6.50 |
| | Acetic Acid | 0.05 | 0.28 |
| | Neotame | 0.54 | 3.00 |
| | Total | 100.00 | 100.00 |

A film was produced by coating the liquid of Example 13 onto a polyester substrate and drying the wet film in a laboratory convection oven for 50 minutes at 70° C. The dry film weight measured 55 mg per 422.4 mm².

Example 14

Ingredients were blended together on an overhead stirrer to form a solution according to Table 9.

TABLE 9

| Example | Excipient | Liquid Mix Concentration (wt %) | Theoretical Dry Deposit Concentration (wt %) |
|---|---|---|---|
| 14 | Ethanol | 63.75 | — |
| | Water | 21.25 | — |
| | Buprenorphine HCl | 4.50 | 30.00 |
| | Hydroxypropylcellulose (M.W. about 80 kDa) | 4.72 | 31.47 |
| | Hydroxypropylcellulose (M.W. about 77 kDa) | 4.72 | 31.47 |
| | Hydroxypropylcellulose (M.W. about 34 kDa) | 1.06 | 7.06 |
| | Total | 100.00 | 100.00 |

Example 15

6 µL of Example 14 solution was microdeposited onto the dried film of Example 13 with a positive displacement pipette. The dispensed liquid was dried in a laboratory convection oven for 20 minutes at 70° C. The surface area of the dried microdeposition was 7.0 mm² and contained 0.182 mg buprenorphine HCl. All units were die-cut to 52.65 mm² and encompassed the 7.0 mm² active deposition.

Example 16

Ingredients were blended together on an overhead stirrer to form a solution according to Table 10.

TABLE 10

| Example | Excipient | Liquid Mix Concentration (wt %) | Theoretical Dry Deposit Concentration (wt %) |
|---|---|---|---|
| 16 | Ethanol | 63.75 | — |
|  | Water | 21.25 | — |
|  | Buprenorphine HCl | 9.00 | 60.00 |
|  | Hydroxypropylcellulose (M.W. about 80 kDa) | 2.70 | 18.00 |
|  | Hydroxypropylcellulose (M.W. about 77 kDa) | 2.70 | 18.00 |
|  | Hydroxypropylcellulose (M.W. about 34 kDa) | 0.60 | 4.00 |
|  | Total | 100.00 | 100.00 |

Example 17

28 µL of Example 16 solution was microdeposited onto the dried film of Example 13 with a positive displacement pipette. The dispensed liquid was dried in a laboratory convection oven for 40 minutes at 70° C. The surface area of the dried microdeposition was 19.6 mm² and contained 2.15 mg buprenorphine HCl. All units were die-cut to 52.65 mm² and encompassed the 19.6 mm² active deposition Example 18

A diffusion study was conducted comparing the permeability of the 52.65 mm² units of Example 15 to the 52.65 mm² units of Example 17. The permeability procedure from Example 6 was followed. As shown in the table of cumulative buprenorphine concentration (ng/cm²/h), the cumulative buprenorphine concentration is greater for Example 17 versus Example 15.

| Average Cumulative Amount (ng/cm²) | | |
|---|---|---|
| Time | Example 17 | Example 15 |
| 1 h | 276,411 | 157,930 |

Example 19

Ingredients were blended together on an overhead stirrer to form a solution according to Table 11.

TABLE 11

| Example | Excipient | Liquid Mix Concentration (wt %) | Dry Film Concentration (wt %) |
|---|---|---|---|
| 19 | Ethanol | 85.00 | |
|  | Ethylcellulose (Viscosity 4-11 cp) | 3.75 | 25.00 |
|  | Ethylcellulose (Viscosity 41-49 cp) | 11.25 | 75.00 |
|  | Total | 100.00 | 100.00 |

A film was produced by coating the liquid of Example 19 onto a polyester substrate and drying the wet film in a laboratory convection oven for 20 minutes at 70° C. The dry film weight measured 53 mg per 10 cm².

Example 20

Ingredients were blended together on an overhead stirrer to form a solution according to Table 12.

TABLE 12

| Example | Excipient | Liquid Mix Concentration (wt %) | Theoretical Dry Deposit Concentration (wt %) |
|---|---|---|---|
| 20 | Ethanol | 20.00 | — |
|  | Water | 60.00 | — |
|  | Apomorphine HCl | 12.75 | 63.76 |
|  | Sodium Metabisulfite | 0.38 | 1.92 |
|  | EDTA | 0.38 | 1.92 |
|  | Hydroxyethylcellulose (M.W. about 90 kDa) | 6.48 | 32.41 |
|  | Total | 99.99 | 100.01 |

Viscosity of the resulting solution from Example 20 was measured on a Brookfield DV-2T LV viscometer at 25° C. using spindle SC4-27 and a shear rate of 1.02 sec⁴. The resulting viscosity was 2,289 cps.

Example 21

22 µL of Example 20 solution was microdeposited onto the dried film of Example 19 with a positive displacement pipette. The dispensed liquid was dried in a laboratory convection oven for 20 minutes at 70° C. The surface area of the dried microdeposition was 20.0 mm² and contained 2.8 mg apomorphine HCl. All units were die-cut to 52.65 mm² and encompassed the 20.0 mm² active deposition.

Example 22

11 µL of Example 20 solution was microdeposited onto the dried film of Example 19 with a positive displacement pipette. The dispensed liquid was dried in a laboratory convection oven for 20 minutes at 70° C. The surface area of the dried microdeposition was 12.6 mm² and contained 1.4 mg apomorphine HCl. All units were die-cut to 52.65 mm² and encompassed the 12.6 mm² active deposition.

Example 23

A diffusion study was conducted comparing the permeability of the 52.65 mm² units of Example 21 to the 52.65 mm² units of Example 22. The permeability procedure from Example 6 was followed. As shown in the table of cumulative apomorphine concentration (ng/cm²/h), the cumulative apomorphine concentration is greater for Example 21 versus Example 22.

| Average Cumulative Amount (ng/cm²) | | |
|---|---|---|
| Time | Example 21 | Example 22 |
| 1 h | 590,764 | 503,980 |

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for forming a dissolvable unit dose film construct, comprising:
  providing a muco-adhesive composition including a muco-adhesive polymer matrix, the muco-adhesive polymer matrix comprising:
    a first water-soluble polymer, a first water-dispersible polymer, a first water-swellable polymer, or combinations thereof; and
    a first liquid carrier;
  drying the muco-adhesive composition to remove at least a portion of the first liquid carrier, forming a muco-adhesive film substrate;
  forming a composition for a first active layer, the composition including a first polymer matrix, the first polymer matrix comprising:
    a second water-soluble polymer, a second water-dispersible polymer, a second water-swellable polymer, or combinations thereof;
    a first active ingredient; and
    a second liquid carrier,
    wherein the composition for the first active layer has a viscosity of 1-300 cps at 1 sec$^{-1}$ shear rate;
  depositing the composition for the first active layer onto the muco-adhesive substrate; and
  removing at least a portion of the second liquid carrier from the deposited composition for the first active layer to form a first dissolvable film active layer on the muco-adhesive substrate.

2. The method of claim 1, wherein the composition for the first active layer is deposited onto the muco-adhesive substrate in a volume in a range between 0.1 µL to 5,000 µL.

3. The method of claim 1, wherein the composition for the first active layer is at least 5% by weight solids at the time of depositing.

4. The method of claim 1, wherein the muco-adhesive polymer matrix further includes a second active ingredient.

5. The method of claim 4, wherein the second active ingredient is compositionally distinct from the first active ingredient.

6. The method of claim 1, further including:
  forming a composition for a second active layer, the composition for the second active layer comprising:
    a second polymer matrix, the second polymer matrix including a third water-soluble polymer, a third water-dispersible polymer, a third water-swellable polymer, or combinations thereof,
    a second active ingredient; and
    a third liquid carrier;
  depositing the composition for the second active layer onto the muco-adhesive substrate; and
  removing at least a portion of the third liquid carrier from the deposited composition for the second active layer, forming a second dissolvable film active layer overlying the muco-adhesive substrate.

7. The method of claim 6, wherein the second dissolvable film active layer is formed on a same face of the muco-adhesive film substrate as the first dissolvable film active layer.

8. The method of claim 7, wherein the second dissolvable film active layer is spatially isolated from the first dissolvable film active layer on the muco-adhesive film substrate.

9. The method of claim 6, wherein the second dissolvable film active layer is formed on an opposing face of the muco-adhesive film substrate from the first dissolvable film active layer.

10. The method of claim 6, wherein the second active ingredient is compositionally distinct from the first active ingredient.

11. The method of claim 6, further including:
  forming a composition for a third active layer, the composition for the third active layer comprising:
    a third polymer matrix comprising a fourth water-soluble polymer, a fourth water-dispersible polymer, a fourth water-swellable polymer, or combinations thereof;
    a third active ingredient; and
    a fourth liquid carrier;
  depositing the composition for the third active layer onto the muco-adhesive substrate; and
  removing at least a portion of the fourth liquid carrier from the deposited composition of the third active layer, forming a third dissolvable film active layer overlying the muco-adhesive film substrate.

12. The method of claim 1, wherein the polymer matrix of the muco-adhesive film substrate and the first dissolvable film active layer include at least one compositionally shared water-soluble polymer, at least one compositionally shared water-dispersible polymer, at least one compositionally shared water-swellable polymer, or combinations thereof.

13. The method of claim 1, wherein the muco-adhesive composition is a thixotropic paste.

14. The method of claim 1, wherein the muco-adhesive film substrate is formed as a continuous web of film, and then is divided into smaller individual films after forming the first dissolvable film active layer on the muco-adhesive film substrate.

15. The method of claim 1, wherein the step of depositing the composition for the first active layer comprises depositing using a jetting system.

16. The method of claim 1, wherein the step of depositing the composition for the first active layer comprises depositing through a piezoelectric or air actuated valve.

17. The method of claim 1, further including cutting the muco-adhesive film substrate to form individual unit doses.

18. The method of claim 1, wherein the first active ingredient comprises at least one of buprenorphine or apomorphine.

19. A unit dose film construct made by the method of claim 1.

20. A method for forming a dissolvable unit dose film construct, comprising:
  providing a muco-adhesive composition including a muco-adhesive polymer matrix, the muco-adhesive polymer matrix comprising:
    a first water-soluble polymer, a first water-dispersible polymer, a first water-swellable polymer, or combinations thereof; and
    a first liquid carrier;
  drying the muco-adhesive composition to remove at least a portion of the first liquid carrier, forming a muco-adhesive film substrate;
  forming a composition for a first active layer, the composition including a first polymer matrix, the first polymer matrix comprising:

a second water-soluble polymer, a second water-dispersible polymer, a second water-swellable polymer, or combinations thereof;
a first active ingredient; and
a second liquid carrier;
depositing the composition for the first active layer onto the muco-adhesive substrate;
removing at least a portion of the second liquid carrier from the deposited composition for the first active layer to form a first dissolvable film active layer on the muco-adhesive substrate;
forming a composition for a second active layer, the composition for the second active layer comprising a second polymer matrix, the second polymer matrix comprising:
a third water-soluble polymer, a third water-dispersible polymer, a third water-swellable polymer, or combinations thereof;
a second active ingredient; and
a third liquid carrier;
depositing the composition for the second active layer onto the muco-adhesive substrate; and
removing at least a portion of the third liquid carrier from the deposited composition for the second active layer, forming a second dissolvable film active layer overlying the muco-adhesive substrate,
wherein the second dissolvable film active layer is formed on an opposing face of the muco-adhesive film substrate from the first dissolvable film active layer.

* * * * *